(12) United States Patent
Hareland

(10) Patent No.: US 11,172,991 B2
(45) Date of Patent: Nov. 16, 2021

(54) NAVIGATION WITH ARBITRARY CATHETER GEOMETRIES AND METHOD OF CONTACT ASSESSMENT

(71) Applicant: Medtronic, Inc., Minneapolis, MN (US)

(72) Inventor: Scott A. Hareland, Lino Lakes, MN (US)

(73) Assignee: Medtronic, Inc., Minneapolis, MN (US)

( * ) Notice: Subject to any disclaimer, the term of this patent is extended or adjusted under 35 U.S.C. 154(b) by 335 days.

(21) Appl. No.: 15/259,782

(22) Filed: Sep. 8, 2016

(65) Prior Publication Data
US 2018/0064495 A1 Mar. 8, 2018

(51) Int. Cl.
*A61B 34/20* (2016.01)
*A61B 5/06* (2006.01)
(Continued)

(52) U.S. Cl.
CPC .............. *A61B 34/20* (2016.02); *A61B 5/065* (2013.01); *A61B 5/066* (2013.01);
(Continued)

(58) Field of Classification Search
CPC . A61B 2018/0022; A61B 34/20; A61B 5/065; A61B 5/066; A61B 18/1492;
(Continued)

(56) References Cited

U.S. PATENT DOCUMENTS

| 6,129,669 A | 10/2000 | Panescu et al. |
| 6,574,498 B1 * | 6/2003 | Gilboa .................... A61B 6/12 |
| | | 600/424 |

(Continued)

FOREIGN PATENT DOCUMENTS

IL WO 2017037705 A1 * 3/2017 ............. A61B 34/20

OTHER PUBLICATIONS

D. Curtis Deno, Haris J. Sih, Stephan P. Miller, Liane R. Teplitsky, and Russ Kuenzi; "Measurement of Electrical Coupling Between Cardiac Ablation Catheters and Tissue"; IEEE Transactions on Biomedical Engineering, vol. 61, No. 3, Mar. 2014 (Year: 2014).*

*Primary Examiner* — Luther Behringer
*Assistant Examiner* — Amy J Shafqat
(74) *Attorney, Agent, or Firm* — Christopher & Weisberg, P.A.

(57) ABSTRACT

A method and system for determining a location of a treatment element relative to an anatomical feature and for estimating contact between the treatment element and the anatomical feature in the context of a navigation system. The system may include a medical device including at least one treatment element and at least one navigation electrode and a navigation system in communication with the one or more navigation electrodes, the navigation system including a processing unit. The processing unit may be programmed to determine a plurality of points that define a surface geometry of the at least one treatment element, calculate a distance between each of the points and a closest point on the anatomical feature, and estimate the likelihood of contact between the points.

13 Claims, 5 Drawing Sheets

(51) Int. Cl.
*A61B 90/00* (2016.01)
*A61B 18/14* (2006.01)
*A61B 18/00* (2006.01)
*A61M 25/01* (2006.01)

(52) U.S. Cl.
CPC .......... *A61B 18/1492* (2013.01); *A61B 90/37* (2016.02); *A61B 5/068* (2013.01); *A61B 2018/0022* (2013.01); *A61B 2018/00345* (2013.01); *A61B 2034/2053* (2016.02); *A61B 2034/2065* (2016.02); *A61B 2090/365* (2016.02); *A61M 2025/0166* (2013.01)

(58) Field of Classification Search
CPC .......... A61B 90/37; A61B 2018/00345; A61B 5/068; A61B 2034/2065; A61B 2017/00867; A61B 2034/102; A61B 2034/2061; A61B 2018/00232; A61B 2034/2072; A61B 2034/302; A61B 2034/2053; A61B 2034/2051; A61M 2025/0166; A61M 2090/365; A61M 2034/2053
See application file for complete search history.

(56) References Cited

U.S. PATENT DOCUMENTS

| | | | |
|---|---|---|---|
| 6,757,557 B1 * | 6/2004 | Bladen | A61B 5/6806 128/899 |
| 6,873,718 B2 | 3/2005 | O'Donnell et al. | |
| 6,926,714 B1 | 8/2005 | Sra | |
| 7,565,190 B2 | 7/2009 | Okerlund et al. | |
| 7,681,579 B2 | 3/2010 | Schwartz | |
| 7,697,972 B2 * | 4/2010 | Verard | A61B 1/00071 600/407 |
| 7,877,128 B2 * | 1/2011 | Schwartz | A61B 18/1492 600/407 |
| 8,046,052 B2 | 10/2011 | Verard et al. | |
| 8,285,021 B2 | 10/2012 | Boese et al. | |
| 2004/0138548 A1 * | 7/2004 | Strommer | A61B 5/0555 600/407 |
| 2005/0256398 A1 | 11/2005 | Hastings et al. | |
| 2007/0152974 A1 | 7/2007 | Kim et al. | |
| 2007/0299352 A1 * | 12/2007 | Harlev | A61B 5/0422 600/509 |
| 2008/0119725 A1 * | 5/2008 | Lloyd | A61B 90/36 600/424 |
| 2008/0221425 A1 | 9/2008 | Olson et al. | |
| 2009/0262109 A1 * | 10/2009 | Markowitz | A61B 5/068 345/419 |
| 2010/0198041 A1 * | 8/2010 | Christian | A61M 25/0074 600/375 |
| 2010/0280363 A1 | 11/2010 | Skarda et al. | |
| 2010/0324414 A1 * | 12/2010 | Harlev | A61B 5/0536 600/424 |
| 2011/0028848 A1 | 2/2011 | Shaquer et al. | |
| 2011/0264039 A1 * | 10/2011 | Thielen | A61M 25/104 604/103.01 |
| 2013/0274712 A1 | 10/2013 | Schecter | |
| 2013/0282005 A1 | 10/2013 | Koch et al. | |
| 2013/0288218 A1 | 10/2013 | Mallin et al. | |
| 2013/0336558 A1 | 12/2013 | Manzke et al. | |
| 2014/0180328 A1 * | 6/2014 | Vaccaro | A61B 17/24 606/196 |
| 2014/0266235 A1 * | 9/2014 | Mathur | G01R 31/025 324/509 |
| 2014/0276108 A1 * | 9/2014 | Vertikov | A61B 5/0084 600/478 |
| 2014/0276712 A1 | 9/2014 | Mallin et al. | |
| 2016/0038252 A1 * | 2/2016 | Barth, Jr. | A61B 34/25 600/424 |
| 2016/0100770 A1 * | 4/2016 | Afonso | A61B 5/0422 600/515 |

* cited by examiner

NAVIGATION WITH ARBITRARY CATHETER GEOMETRIES AND METHOD OF CONTACT ASSESSMENT

CROSS-REFERENCE TO RELATED APPLICATION n/a

STATEMENT REGARDING FEDERALLY SPONSORED RESEARCH OR DEVELOPMENT n/a

TECHNICAL FIELD

The present invention relates to a method and system for determining a location of a treatment element of a medical device and for estimating contact between the treatment element and tissue in the context of a navigation system.

BACKGROUND

In many non-invasive or minimally invasive surgical and treatment procedures, navigating a medical device within a patient's body can be very challenging. Navigation systems are frequently used to help the user identify the location of the medical device and to steer the medical device to the target treatment location. For example, navigation is an important tool in many electrophysiological (EP) procedures because it helps the user understand the placement of the medical device within the cardiac space. Additionally, navigation is often used to place medical devices at areas targeted for thermal treatment and/or ablation.

In many navigation systems, a medical device includes navigation electrodes, which can be detected by the system by a variety of means. The position of these navigation electrodes can be displayed to the user relative to an anatomical structure, such as the endocardial surface of the heart. This navigation capability allows the user to position the medical device relative to the target tissue and subsequently document activity, such as the application of ablative therapy, at that location.

When the medical device is a focal catheter, for instance, the ablating surface may be directly imaged on the navigation system and there is a close, sometimes direct, coupling between the navigation and the delivered therapy. However, navigation electrodes other medical devices, such as balloon catheters, may not exactly correlate with the ablating surface (e.g., the surface of the balloon). Thus, it may be difficult to accurately determine the location of the balloon ablating surface using a traditional navigation system. Additionally, although including additional navigation electrodes on the device may help locate the device, doing so poses new challenges for catheter design, manufacture, and steering, to name a few.

SUMMARY

The method and system disclosed herein allows for determination of a location of a treatment element relative to an anatomical feature and for estimation of contact between the treatment element and the anatomical feature in the context of a navigation system. In one embodiment, a system for determining a location of a medical device relative to an anatomical feature includes: a medical device including: an elongate body having a distal portion, a proximal portion, and a longitudinal axis; at least one treatment element coupled to the elongate body distal portion, the at least one treatment element having a surface geometry; and at least one navigation electrode coupled to the elongate body distal portion. The system also includes a navigation system in communication with the at least one navigation electrode, the navigation system including a processing unit having processing circuitry configured to: determine a first surface of the anatomical feature; determine a spatial location of each of the at least one navigation electrode; calculate the surface geometry of the at least one treatment element; define a plurality of points on the surface geometry of the at least one treatment element; for each of the plurality of points on the surface geometry of the at least one treatment element, define a point on the first surface of the anatomical feature that is closest to a corresponding point of the plurality of points on the surface geometry of the at least one treatment element; and for each defined point on the first surface of the anatomical feature, estimate a likelihood of contact between the defined point on the first surface of the anatomical feature and a corresponding point of the plurality of points on the surface geometry of the at least one treatment element.

In one embodiment, the medical device includes a first navigation electrode and a second navigation electrode.

In one embodiment, the first navigation electrode is distal to the at least one treatment element and the second navigation electrode is proximal to the at least one treatment element.

In one embodiment, the at least one treatment element is an expandable treatment element.

In one embodiment, the expandable treatment element is a substantially spherical balloon, the processing circuitry being configured to calculate the surface geometry of the balloon according to the equation:

$$S_b = f_1(p_1, p_2, R, \theta, \varphi) \quad (1)$$

where $p_1$ is a location of the first navigation electrode and $p_2$ is a location of the second navigation electrode.

In one embodiment, the expandable treatment element is a substantially cylindrical balloon, the processing circuitry being configured to calculate the surface geometry of the balloon according to the equation:

$$S_c = f_2(p_1, p_2, R, \theta, z) \quad (2)$$

where $p_1$ is a location of the first navigation electrode and $p_2$ is a location of the second navigation electrode.

In one embodiment, the at least one treatment element is an expandable array of electrodes, the processing circuitry being configured to calculate the surface geometry of the expandable array of electrodes according to the equation:

$$S_x = f_3(p_1, p_2, x_n, y_n, z_n) \quad (3)$$

where $p_1$ is a location of the first navigation electrode, $p_2$ is a location of the second navigation electrode, and n is a value sufficient to represent the surface geometry of the expandable array of electrodes.

In one embodiment, the at least one treatment element is a plurality of treatment elements located over a linear distance, the processing circuitry being configured to calculate the surface geometry of the plurality of treatment elements located over a linear distance according to the equation:

$$S_l = f_3(p_1, p_2, g_1(p_1, p_2), g_2(p_1, p_2), g_3(p_1, p_2)) \quad (4)$$

where $p_1$ is a location of the first navigation electrode and $p_2$ is a location of the second navigation electrode.

In one embodiment, the processing circuitry is further configured to store an anatomical image of an area including the anatomical feature.

In one embodiment, the processing circuitry is configured to determine the first surface of the anatomical feature based on the anatomical image.

In one embodiment, the processing circuitry is further configured to determine a second surface of the anatomical feature, the second surface being opposite the first surface, the processing circuitry being configured to determine the first surface based on the second surface.

In one embodiment, the processing circuitry is configured to determine the first surface by transforming the second surface according to the equation:

$$[S_1]=[M][S_2] \quad (5)$$

where M is a transform.

In one embodiment, the processing circuitry is configured to estimate the likelihood of contact by assigning a value to each defined point on the first surface of the anatomical feature, the value being one of highly probable contact, likely contact, and no contact.

In one embodiment, the processing circuitry is configured to: assign a value of highly probable contact to a defined point on the first surface of the anatomical feature when a distance between the defined point on the first surface of the anatomical feature and the nearest point of the plurality of points on the surface geometry of the at least one treatment element is less than a first predetermined distance; and assign a value of likely contact to a defined point on the first surface of the anatomical feature when a distance between the defined point on the first surface of the anatomical feature and the nearest point of the plurality of points on the surface geometry of the at least one treatment element is between the first predetermined distance and a second predetermined distance, the first predetermined distance being less than the second predetermined distance.

In one embodiment, the first predetermined distance is 0.5 mm and the second predetermined distance is 1.0 mm.

In one embodiment, the processing circuitry is configured to estimate the likelihood of contact by assigning a value on a continuous scale to each defined point on the first surface of the anatomical feature, the value being one of: a minimum value indicating no contact; a maximum value indicating definite contact; and an intermediate value between the minimum value and the maximum value along the continuous scale, the intermediate value indicating possible contact with a varying degree of certainty.

In one embodiment, a system for determining a location of a medical device relative to an anatomical feature includes: a medical device including: an elongate body having a distal portion, a proximal portion, and a longitudinal axis; at least one treatment element coupled to the elongate body distal portion, the at least one treatment element having a surface geometry; and a first navigation electrode coupled to the elongate body distal portion distal to the at least one treatment element and a second navigation electrode coupled to the elongate body distal portion proximal to the at least one treatment element. The system also includes a navigation system in communication with the at least one navigation electrode, the navigation system being configured to store an anatomical image of an area including the anatomical feature, the navigation system including a processing unit having processing circuitry with a memory and a processor, the memory in communication with the processor and having instructions that, when executed by the processor, configure the processor to: determine a first surface of the anatomical feature and a second surface of the anatomical feature that is opposite the first surface, the processor being configured to determine the first surface based on one of: the anatomical image; and transformation of the second surface; determine a spatial location of each of the at least one navigation electrode; calculate the surface geometry of the at least one treatment element; define a plurality of points on the surface geometry of the at least one treatment element; for each of the plurality of points on the surface geometry of the at least one treatment element, define a point on the first surface of the anatomical feature that is closest to a corresponding point of the plurality of points on the surface geometry of the at least one treatment element; and for each defined point on the first surface of the anatomical feature, estimate a likelihood of contact between the defined point on the first surface of the anatomical feature and a corresponding point of the plurality of points on the surface geometry of the at least one treatment element, the estimation being one of: a minimum value indicating no contact; a maximum value indicating definite contact; and an intermediate value between the minimum value and the maximum value along a continuous scale, the intermediate value indicating possible contact with a varying degree of certainty, with the degree of certainty being less when the intermediate value is closer to the minimum value than when the intermediate value is closer to the maximum value.

In one embodiment, a method for determining a location of a medical device relative to an anatomical feature includes: providing an anatomical image of an area including the anatomical feature; providing a medical device, the medical device including at least one treatment element and at least one navigation electrode, the at least one treatment element having a surface geometry and each of the at least one navigation electrode being at a known location relative to the surface geometry; determining a surface of the anatomical feature based at least in part on the anatomical image; determining a spatial location of each of the at least one navigation electrode relative to the surface of the anatomical feature; calculating the surface geometry of the at least one treatment element; defining a plurality of points on the surface geometry of the at least one treatment element; for each of the plurality of points on the surface geometry of the at least one treatment element, defining a point on the first surface of the anatomical feature that is closest to a corresponding point of the plurality of points on the surface geometry of the at least one treatment element; and for each defined point on the surface of the anatomical feature, estimating a likelihood of contact between the defined point on the first surface of the anatomical feature and a corresponding point of the plurality of points on the surface geometry of the at least one treatment element.

In one embodiment, estimating the likelihood of contact includes assigning a value to each defined point on the first surface of the anatomical feature, the value being one of: highly probable contact; likely contact; and no contact.

In one embodiment, assigning a value to each defined point on the first surface includes: assigning the value of highly probable contact to a defined point on the first surface of the anatomical feature when a distance between the defined point on the first surface of the anatomical feature and the nearest point of the plurality of points on the surface geometry of the at least one treatment element is less than a first predetermined distance; and assigning a value of likely contact to a defined point on the first surface of the anatomical feature when a distance between the defined point on the first surface of the anatomical feature and the nearest point of the plurality of points on the surface geometry of the at least one treatment element is between the first predetermined distance and a second predetermined distance, the first predetermined distance being less than the second predetermined distance.

In one embodiment, the method further includes: providing a database containing geometrical information about the surface geometry of the at least one treatment element; and parameterizing the surface geometry of the at least one treatment element based on the geometrical information.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein.

DETAILED DESCRIPTION

Figure 1A:
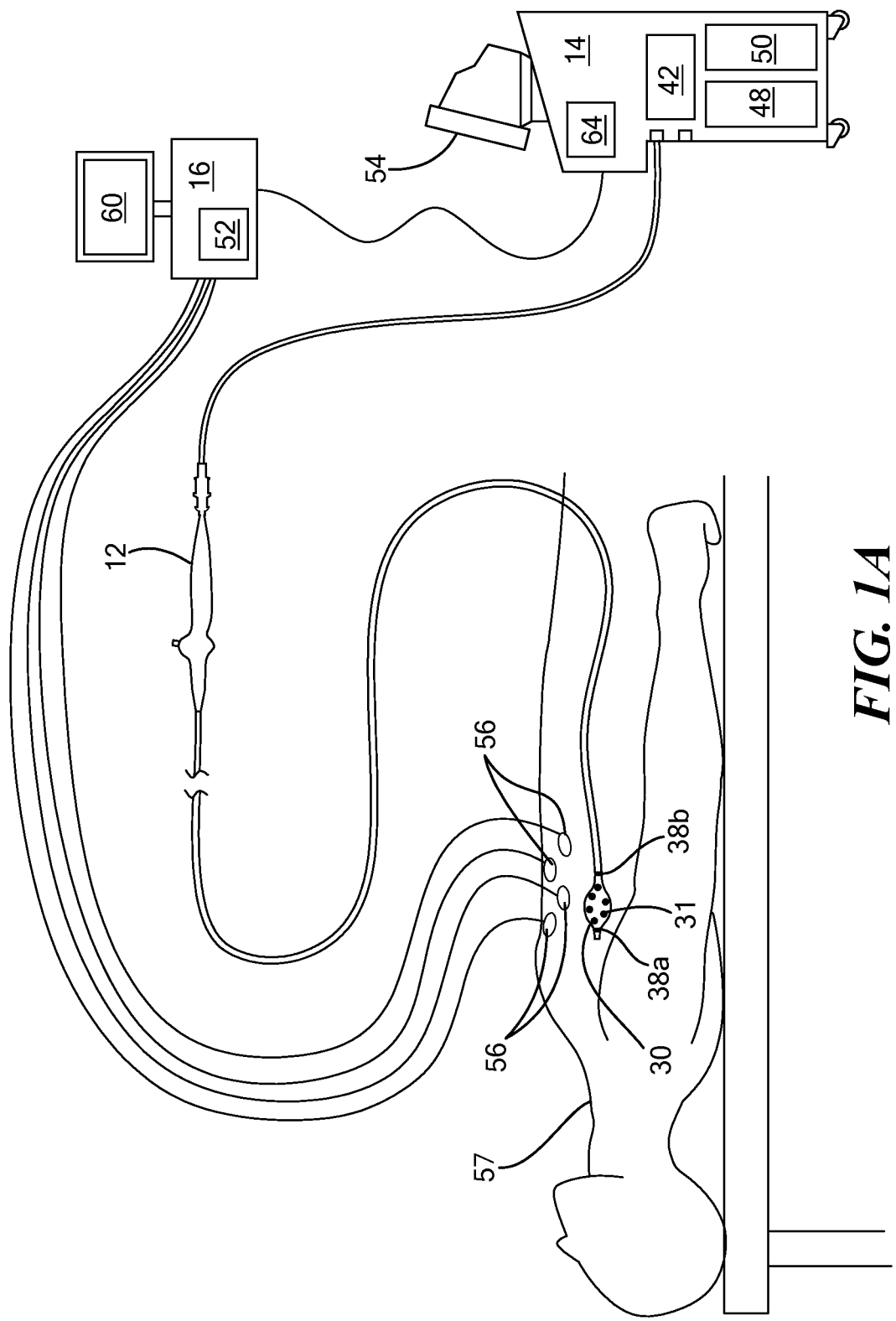
FIGS. 1A and 1B show an exemplary medical system that includes a medical device having an expandable treatment element.

The method and system disclosed herein allows for determination of a location of a treatment element relative to an anatomical feature and for estimation of contact between the treatment element and the anatomical feature in the context of a navigation system. Generally speaking, the system may include a medical device including at least one treatment element and at least one navigation electrode and a navigation system in communication with the one or more navigation electrodes, the navigation system including a processing unit. The processing unit may be programmed to determine a plurality of points that define a surface geometry of the at least one treatment element, calculate a distance between each of the points and a closest point on the anatomical feature, and estimate the likelihood of contact between the points. The method may include determining a plurality of points that define a surface geometry of an at least one treatment element of a medical device, calculating a distance between each of the points and a closest point on the anatomical feature, and estimating the likelihood of contact between the points.

Before describing in detail exemplary embodiments that are in accordance with the disclosure, it is noted that components have been represented where appropriate by conventional symbols in drawings, showing only those specific details that are pertinent to understanding the embodiments of the disclosure so as not to obscure the disclosure with details that will be readily apparent to those of ordinary skill in the art having the benefit of the description herein.

As used herein, relational terms, such as "first," "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

Figure 1B:
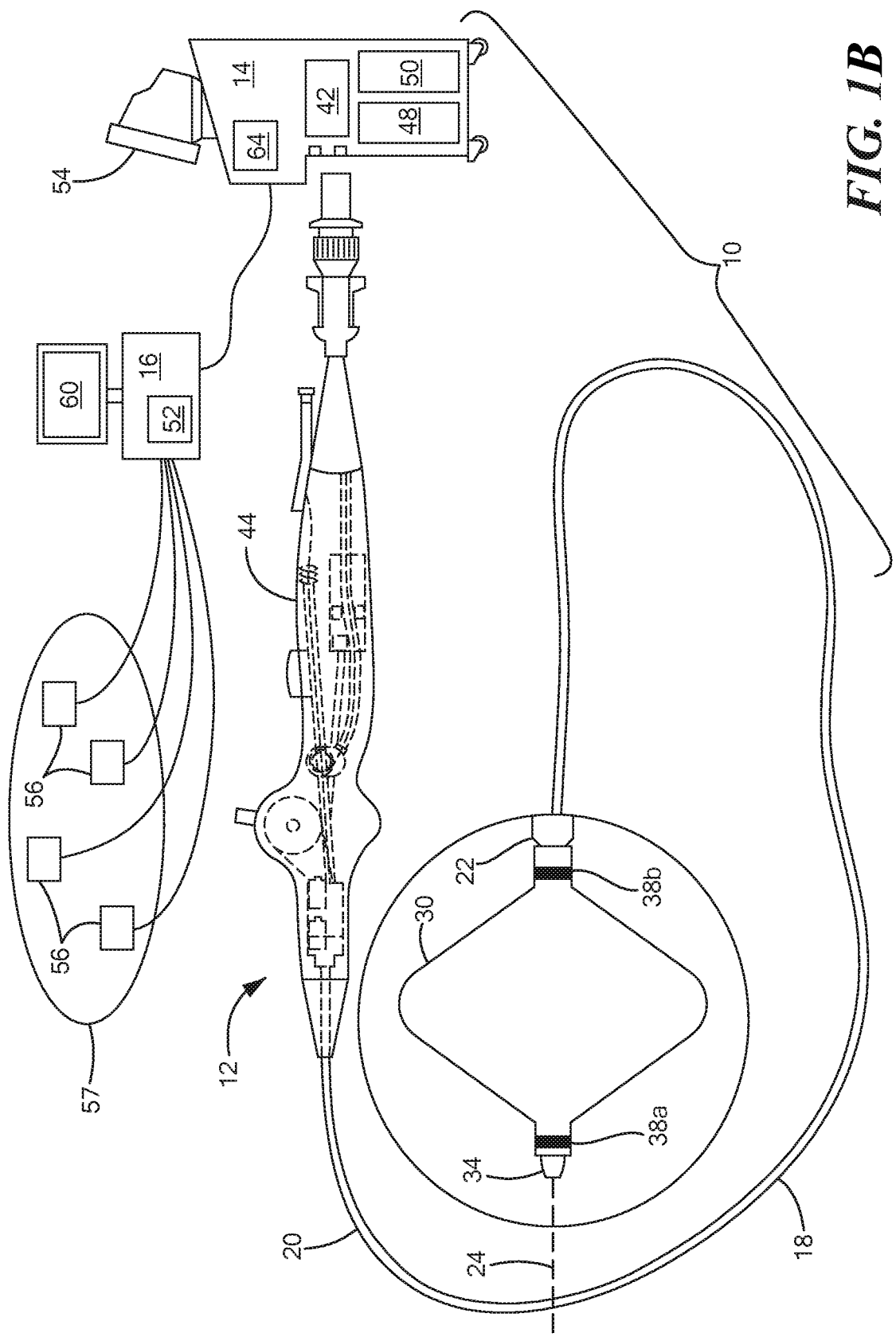

Referring now to the drawing figures in which like reference designations refer to like elements, an embodiment of a medical system constructed in accordance with the principles of the present invention is shown in FIGS. 1A and 1B, generally designated as "10." The system 10 generally includes a medical device 12 that may be coupled to a control unit 14 or operating console and a navigation system 16 in communication with the device 12 and the control unit 14. The medical device 12 may generally include one or more diagnostic or treatment elements for energetic, therapeutic, and/or investigatory interaction between the medical device 12 and a treatment site or region. The diagnostic or treatment region(s) may deliver, for example, cryogenic therapy, thermal energy, radiofrequency energy, ultrasound energy, laser energy, or other energetic transfer with a tissue area in proximity to the treatment region(s), including cardiac tissue.

The medical device 12 may be a treatment and/or mapping device. Broadly, the device 12 may be any catheter, medical device, or insertable element requiring visualization on a navigation system. The medical device 12 may include an elongate body 18 passable through a patient's vasculature and/or proximate to a tissue region for diagnosis or treatment. For example, the device 12 may be a catheter that is deliverable to the tissue region via a sheath or intravascular introducer (not shown). The elongate body 18 may define a proximal portion 20, a distal portion 22, and a longitudinal axis 24, and may further include one or more lumens disposed within the elongate body 18 thereby providing mechanical, electrical, and/or fluid communication between the elongate body proximal portion 20 and the elongate body distal portion 28.

The medical device 12 may further include one or more treatment elements 30 at, coupled to, or on the elongate body distal portion 22. In the non-limiting embodiment shown in FIGS. 1A and 1B, the device may include a treatment element 30 that is expandable, such as one or more balloons. However, it will be understood that the device may include one or more treatment elements 30 that are not expandable. For example, the device 12 may be a focal catheter that includes one or more electrodes on the distal portion 22, and each electrode may be considered to be a treatment element 30. Even if the device 12 includes an expandable treatment element, the device 12 may also include one or more treatment electrodes on the expandable treatment element, the catheter body, and/or other suitable locations, even though treatment electrodes are not shown in the figures. Further, the medical device 12 may have a configuration that provides complex geometry to the treatment element(s). For example, instead of an expandable balloon, the medical device 12 may include one or more carrier arms bearing the treatment element(s).

The expandable treatment element 30 of the system shown in FIG. 1B may be coupled to a portion of the elongate body distal portion 22. The device may optionally include a shaft that is slidably disposed within the elongate body 18 and at least a portion of the shaft may be located within the expandable treatment element 30. The shaft may further include or define a distal tip 34 that may protrude beyond the distal end of the expandable treatment element 30. The expandable treatment element 30 may further include one or more material layers providing for puncture resistance, radiopacity, or the like. If the device 12 is used to delivery cryotherapy (or if used with another energy modality that requires fluid to be delivered to the inner chamber of the treatment element 30), the device may also include one or more fluid injection elements. A device having a non-expandable treatment element may also include one or more fluid injection elements within the elongate body 18 proximate the one or more treatment elements 30 (for example, treatment electrode(s)). Further, if the device 12 is used or mapping in addition to or instead of for the delivery of treatment, the device 12 may include one or more mapping electrodes. Although the term "treatment element" is used herein, it will be understood that a mapping element or mapping electrodes could be used instead.

As is discussed in more detail below, the device 12 may also include one or more navigation electrodes 38 that are used by the navigation system 16 to visualize the device 12 on a control unit display and/or a navigation system display. For example, the device 12 shown in FIGS. 1A and 1B may include a first navigation electrode 38a distal to the expandable portion of the treatment element 30 and a second navigation electrode 38b proximal to the expandable portion of the treatment element 30. Although the navigation electrodes 38a, 38b are shown as being coupled to the portion of the treatment element 30 that is coupled to the elongate body and/or shaft of the device, the navigation electrodes 38a, 38b could alternatively be located distal and proximal to all portions of the treatment element. Additionally, the device may include more or fewer navigation electrodes 38 than are shown in FIGS. 1A and 1B. Regardless of the number, configuration, or location of the navigation electrode(s) 38, each navigation electrode 38 is a known distance from, or location relative to, the treatment element(s) 30.

Each treatment electrode (if included) and navigation electrode 38 may be electrically conductive segments for conveying an electrical signal, magnetic signal, current, or voltage to a designated tissue region and/or for measuring, recording, receiving, receiving, assessing, or otherwise using one or more electrical properties or characteristics of surrounding tissue or other electrodes. The electrodes may be configured in a myriad of different geometric configurations or controllably deployable shapes, and may also vary in number to suit a particular application, targeted tissue structure or physiological feature.

If the treatment element(s) 30 includes treatment electrodes, each treatment electrode may be electrically coupled to an output portion of a power source 42, such as a radiofrequency energy generator or other type of energy generator, and may be in electrical communication with the control unit 14. Each navigation electrode 38 may also be in communication with the navigation system 16 and the control unit 14, and may be configured to receive magnetic or electric signals from the navigation system and transmit signals to the control unit 14 and/or navigation system 16 in a wired and/or wireless connection.

The system 10 may include one or more sensors to monitor the operating parameters throughout the system, including for example, pressure, temperature, flow rates, volume, power delivery, impedance, or the like in the control unit 14 and/or the medical device 12, in addition to monitoring, recording or otherwise conveying measurements or conditions within the medical device 12 or the ambient environment at the distal portion of the medical device 12. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the lumens/fluid paths of the medical device 12. Such valves, controllers, or the like may be located in a portion of the medical device 12 and/or in the control unit 14.

The medical device 12 may include a handle 44 coupled to the elongate body proximal portion 20. The handle 44 may include circuitry for identification and/or use in controlling of the medical device 12 or another component of the system. Additionally, the handle 44 may also include connectors 46 that are mateable to the control unit 14 to establish communication between the medical device 12 and one or more components or portions of the control unit 14. The handle 44 may also include one or more actuation or control features that allow a user to control, deflect, steer, or otherwise manipulate a distal portion of the medical device 12 from the proximal portion of the medical device 12. For example, the handle 44 may include one or more components such as a lever or knob 46 for manipulating the elongate body 18 and/or additional components of the medical device 12.

As used herein, the term "control unit 14" for simplicity may include any system components that are not part of the medical device 12 itself, other than components of the navigation system, regardless of whether the component is physically located within or external to the control unit 14. Further, the navigation system 16 may be a standalone system in communication with the control unit 14 or may be contained within or integrated with the control unit 14, even though it is shown as being physically separated from the control unit in FIGS. 1A and 1B. The control unit 14 may include one or more components for the delivery of one or more energy modalities for which the system is used. For example, if the system 10 is used to deliver cryotherapy, the control unit 14 may include a supply 48 of a fluid such as a coolant, cryogenic refrigerant, or the like, an exhaust or scavenging system for recovering or venting expended fluid for re-use or disposal, as well as various control mechanisms. In addition to providing an exhaust function for the fluid or coolant supply 48, the control unit 14 may also include pumps, valves, controllers or the like to recover and/or re-circulate fluid delivered to the handle 44, the elongate body 18, and/or the fluid pathways of the medical device 12. Further, a vacuum pump 50 in the control unit 14 may create a low-pressure environment in one or more conduits within the medical device 12 so that fluid is drawn into the conduit(s)/lumen(s) of the elongate body 18, away from the distal portion 22 and towards the proximal portion 20 of the elongate body 18. Additionally or alternatively, the control 14 unit may include a radiofrequency generator or power source 42 as a treatment or diagnostic mechanism in communication with treatment electrode(s) of the medical device 12. The radiofrequency generator 42 may have a plurality of output channels, with each channel coupled to an individual treatment electrode. The radiofrequency generator 42 may be operable in one or more modes of operation.

The control unit 14 may include one or more controllers, processors, and/or software modules 52 containing circuitry configured to execute instructions or algorithms to provide for the automated operation and performance of the features, sequences, calculations, or procedures described herein. For example, the processor(s) 52 may be configured, programmed, or programmable to perform the calculations and make the determinations discussed in greater detail below to identify a target location for a medical device relative to an anatomical feature, even if that device has complex geometry that has traditionally made the process challenging. Further, the control unit 14 may include one or more user input devices, controllers, and displays 54 for collecting and conveying information from and to the user.

The navigation system 16 may be any commercially available navigation system suitable for use with the control unit 14, device 12, and type of procedure. As a non-limiting example, the navigation system 16 may include a plurality of surface electrodes 56, a reference electrode (not shown), and a processing unit 58 that collects and processes signals from the navigation electrodes 38, and a display that displays to the user the location of the device 12 within the patient's body 57 and/or relative to the target anatomical feature (for example, a pulmonary vein ostium), and recommended landing zones for the device 12. The processing unit 58 may include processing circuitry including a memory and a processor, the memory in communication with the processor and having instructions that, when executed by the processor, configure the processor to perform the calculations and determinations discussed herein. Additionally or alternatively, this information may be displayed on the display 64 of the control unit 14. The navigation system 16 may also include an energy generator (not shown) for delivering energy to the plurality of surface electrodes 56. Alternatively, the navigation system may be in communication with the control unit power source 42. It will be understood that the calculations discussed herein may additionally or alternatively be performed by one or more processors 64 within the control unit 14.

As shown in FIGS. 1A and 1B, the surface electrodes 56 may be applied to the patient's skin and may deliver relatively low-frequency radiofrequency energy through the patient toward the procedure site, current device location, or the target anatomical feature. The navigation electrode(s) 38 on the device 12 may each record a voltage and impedance from this energy and transmit data to the processing unit 58, which may then determine a position of the electrode(s) 38, and therefore the device 12, within the patient. The processing unit 58 may perform this calculation many times during a procedure, frequently updating the registered location and displaying such to the user so the user can visualize the location of the device relative to the target anatomical feature in real time. However, it will be understood that the navigation electrode(s) 38 may be configured to be used with navigation systems other than impedance-based systems, such as navigation systems that are magnetic field based, hybrid impedance/magnetic field based, ultrasound field based, and/or radiation based.

The navigation system 16 may be configured to receive, store, manipulate, display, or otherwise use a digital image of the anatomical structure including the target treatment area. The image may be obtained using an imaging system 68, such as a computed tomography (CT) system, a magnetic resonance imaging (MRI) system, or other system suitable for creating images of locations within a patient's body. For example, the imaging system 68 may create images in Digital Imaging and Communications in Medicine (DICOM) format. The imaging system 68 may be in communication with and digitally transmit images to the navigation system 16 and/or the control unit 14 for further processing. Additionally or alternatively, images recorded by the imaging system 68 may be recorded and transferred to the navigation system 12 and/or the control unit 14 by a user.

Figure 2:
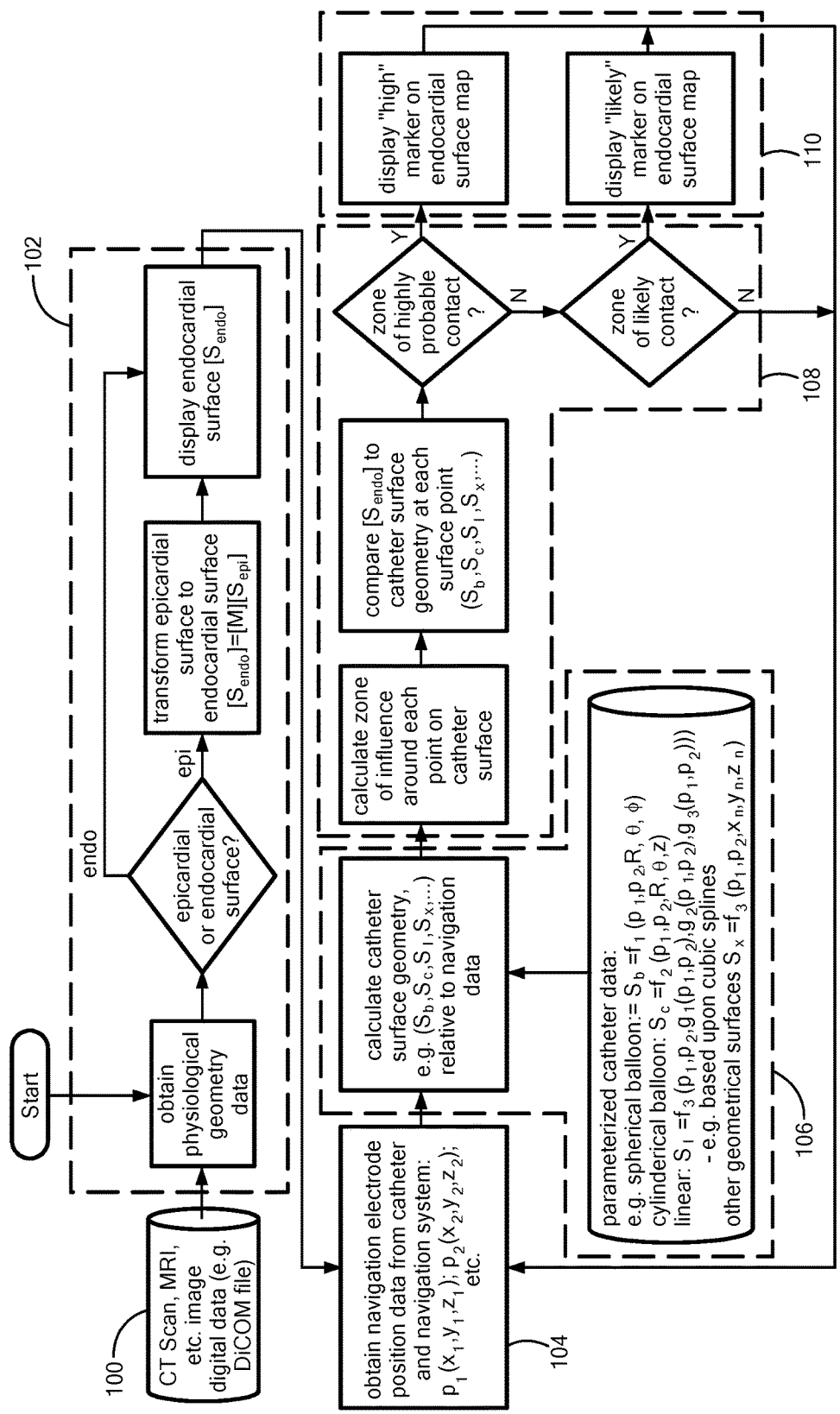
FIG. 2 shows a schematic representation of a method for locating a medical device relative to a target tissue structure.

Now referring to FIG. 2, a schematic representation of a method for locating a medical device relative to a target tissue structure is shown. The system 10 may identify one or more target anatomical features, such as pulmonary vein(s), prior to or during the procedure. A target pulmonary vein ostium, for example, may be manually defined by the user or automatically or semi-automatically defined by the control unit 14 or navigation system 16 using an algorithm executed by the processor(s) 64 or processing unit 58. When executed, the algorithm may be used to estimate a location of the device 12 relative to the anatomical structure and quality of contact between target tissue and the treatment element 30.

The process performed by the processing unit 58 of the navigation system 16 is now discussed in more detail. However, if the algorithm for the initial identification of the target anatomical feature is executed by the processor(s) 64 of the control unit 14, this information will be transmitted from the control unit 14 to the navigation system 16, which may then perform the calculations/execute further algorithm(s) for determining the optimal device position for the procedure.

As an initial step, a digital anatomical image (for example, a DICOM file) may be transmitted to, uploaded to, or otherwise made accessible to the navigation system 16 (Step 100). The image may be of a particular structure that includes the target anatomical feature. In the next step, the surface geometry may be determined. As a non-limiting example, the structure that will be referred to in describing the method may be a heart and the target anatomical feature may be a left atrial wall. However, it will be understood that this method may be used for other structures and anatomical features as well. In Step 102, the processing unit 58 may determine endocardial first surface $S_{endo}$ and its geometry from the image. Additionally or alternatively, the processing unit 58 may infer the endocardial surface $S_{endo}$ from an epicardial second surface $S_{epi}$ image using a suitable transform M according to the following equation:

$$[S_{endo}] = [M][S_{epi}] \tag{1}$$

Put another way, the processing unit 58 may apply a transform M to the epicardial surface $S_{epi}$ in the image to estimate the endocardial surface $S_{endo}$. The endocardial surface may then be displayed on the navigation system display 60 and/or the control unit display 54.

The medical device 12 may then be navigated through the patient's body and into the heart. The navigation system 16 may detect the navigation electrode(s) 38 and the processing unit 58 may determine the spatial location of each navigation electrode 38 (Step 104) within the heart using the navigation system 16. For example, the location may be defined with Cartesian coordinates (e.g., $p_1(x_1, y_1, z_1)$, $p_2(x_2, y_2, z_2)$, etc.); however, it will be understood that any other system of defining a location may additionally or alternatively be used.

In the next step, the processing unit 58 may calculate the surface geometry of the medical device treatment element(s) 30 relative to navigation electrode data 38 (Step 106). If the treatment element 30 is a balloon, the surface geometry may be the geometry of the outer surface of the balloon. If the treatment element(s) 30 are arranged in a linear pattern (for example, if the device is a focal catheter or a multi-electrode linear or non-linear device), the surface geometry may be the geometry of the length of the device body 18 over which the treatment element(s) 30 are located. The treatment element(s) 30 may be arranged in a more complex configuration, such as may be the case for devices having an expandable electrode array 31 as shown in FIG. 1A. In this case, the surface geometry may be a geometry of an imaginary surface that includes all the treatment element(s) 30. The processing unit 58 may access a database containing geometrical information about the surface geometry of the particular treatment element 30 used on the device 12 relevant to the navigation electrode(s) 38. The database may be stored within the navigation system 16, the control unit 14, and/or in a component external to the navigation system 16 and/or the control unit 14. This data may be used to parameterize the surface geometry of the treatment element(s). For example, the processing unit 58 may parameterize a substantially spherical treatment element ($S_b$) 30, such as a balloon, as a function of geometrical variables such as $R(\theta, \varphi)$, $\theta$, $\varphi$ to map the surface extent of the treatment element 30 relative to the navigation electrode(s) 38:

$$S_b = f_1(p_1, p_2, R, \theta, \varphi) \quad (2)$$

Likewise, if the treatment element 30 has a geometry that may conveniently be expressed in cylindrical coordinates (for example, an elongated, substantially cylindrical balloon), the processing unit 58 may use the geometrical variables (R, $\theta$, z), where z may be expressed relative to the navigation electrode(s) 38 (for example, $p_1$ and $p_2$) rather than the absolute coordinate system of $S_{endo}$:

$$S_c = f_2(p_1, p_2, R, \theta, z) \quad (3)$$

As a further example, the processing unit 58 may use a combination of cubic splines or other functions for a device 12 with one or more treatment element(s) 30 over a region with linear geometry (for example, a focal catheter), and the number of navigation electrode(s) 38 on the device 12 should be sufficient to uniquely reflect the location of the linear segment:

$$S_l = f_3(p_1, p_2, g_1(p_1, p_2), g_2(p_1, p_2), g_3(p_1, p_2)) \quad (4)$$

where g is a predetermined curve fit for the structure. The values for g may be determined based on the device construction and/or shape the device takes based on the location of the navigation electrodes. The variable g is representative of any number of geometric points along the cubic splines. Therefore, $g_1$, $g_2$, and $g_3$ are representative of the number of navigation electrodes 38 used on the device 12. Additionally, variables $f_1$, $f_2$, and $f_3$ indicate functions of the variables within the parentheses. For example, $f_1$ is a first function, $f_2$ is a second function, and $f_3$ is a third function.

In other cases, the geometry of the device 12 may be expressed entirely as a set of points (e.g., $(x_n, y_n, z_n)$ relative to the navigation electrode(s) 38 where the index n can be chosen to be any arbitrary value sufficient to adequately represent the catheter surface:

$$S_x = f_3(p_1, p_2, x_n, y_n, z_n) \quad (5)$$

As a non-limiting example, this calculation may be used for devices in which the treatment element is an expandable array 31 of electrodes, a balloon with non-spherical or non-cylindrical geometry, and for other devices having a non-uniform treatment element or array 31 of treatment elements.

The processing unit 58 may now analyze each point on the surface of the treatment element(s) 30 and/or surface geometry of an area including treatment element(s) (for example, in the case of a device having an expandable electrode array 31 or a focal catheter having a length over which treatment element(s) are located) to determine a distance to the nearest point on the endocardial surface $S_{endo}$ (Step 108). At each point, a zone of influence may be used to estimate the likelihood of contact between the treatment element(s) 30 and the endocardial surface. For example, the zone of influence may be chosen such that a distance of less than a first predetermined amount (for example, 0.5 mm) between the treatment element(s) 30 and its nearest point on the endocardial surface $S_{endo}$ would be labeled as "highly probable contact" and a second predetermined amount (for example, between 0.5 mm and 1.0 mm) would be labeled as "likely contact." Other points not labeled as "highly probable contact" or "likely contact" may be labeled as "no contact" for simplicity, even if there is a small likelihood of contact. The zones of influence of each contact indicator may be displayed as isolines 77, 79, and 81 in the endocardial surface map 72.

Alternatively, contact assessment could be based on a continuous scale instead of the ordinal scale disclosed immediately above. As a non-limiting example, the scale may begin at a minimum value (for example, 0) indicating no contact, and end at a maximum value (for example, 100) indicating definite contact. The intermediate values between the minimum and maximum values may represent all levels of confidence between a determination of "no contact" and a determination of "definite contact." The intermediate values and associated indications of contact may also be based on distance between a point on the treatment element(s) 30 and its nearest point on the endocardial surface $S_{endo}$, which each value being displayed as an isoline 77, 79, and 81 in the endocardial surface map 72. Intermediate values may indicate possible contact with a varying degree of certainty. For example, a value indicating possible contact with a high degree of certainty (that is, closer to the maximum value of the continuous scale) may be interpreted as equivalent to an ordinal value of "highly likely contact." Although the values on the continuous scale may be presented to the user in the same way as the values in the ordinal scale, but using the continuous scale may enable the system to communicate to the user a larger number of contact indicators. Nuances in the areas represented by the contact indicators may help the user better understand the overall state of contact between the endocardial surface $S_{endo}$ and the treatment element(s) 30.

Further, the zone of influence may be adjusted for various aspects of the navigation system 16. For example, the zone of influence may be adjusted to compensate for the accuracy of the navigation positioning system itself, if the navigation positioning system accuracy were to be less than ideal.

The processing unit 58 may then augment the endocardial surface $S_{endo}$ and display an adjusted endocardial surface map 72 on the navigation system display 60 and/or control unit display 54 to graphically distinguish the different points of treatment element-to-tissue contact. For example, physical points of contact and estimated contact quality (zone of influence) as described above may be displayed and graphically distinguished using markers, for example, different colors, shading, symbols, or the like. Points identified as being within a zone of highly probable contact may be identified on the endocardial surface map 72 with "high probability" markers (for example, by color, shading, symbols, or the like) and points identified as being within a zone of likely contact may be identified on the endocardial surface map 72 with "likely" markers (Step 110).

Figure 3:
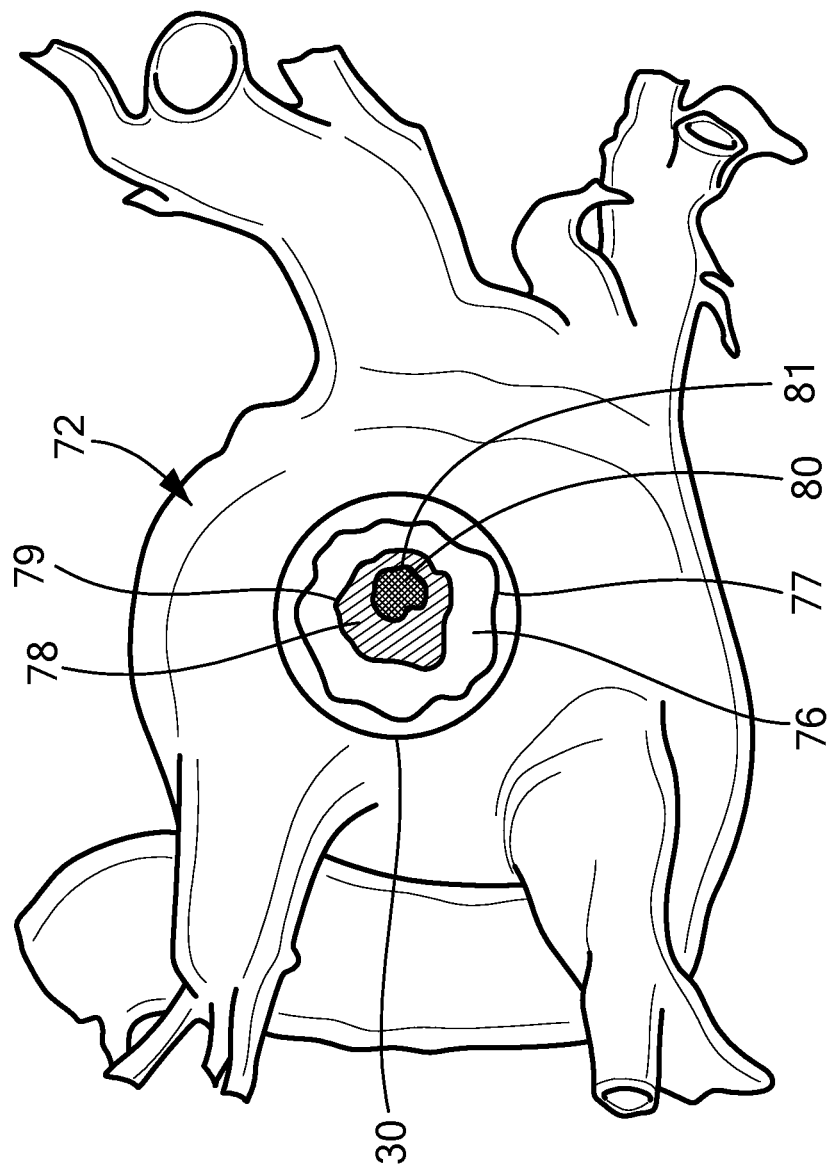
FIGS. 3 and 4 show an exemplary graphical display of areas of device contact on an endocardial surface.
Figure 4:
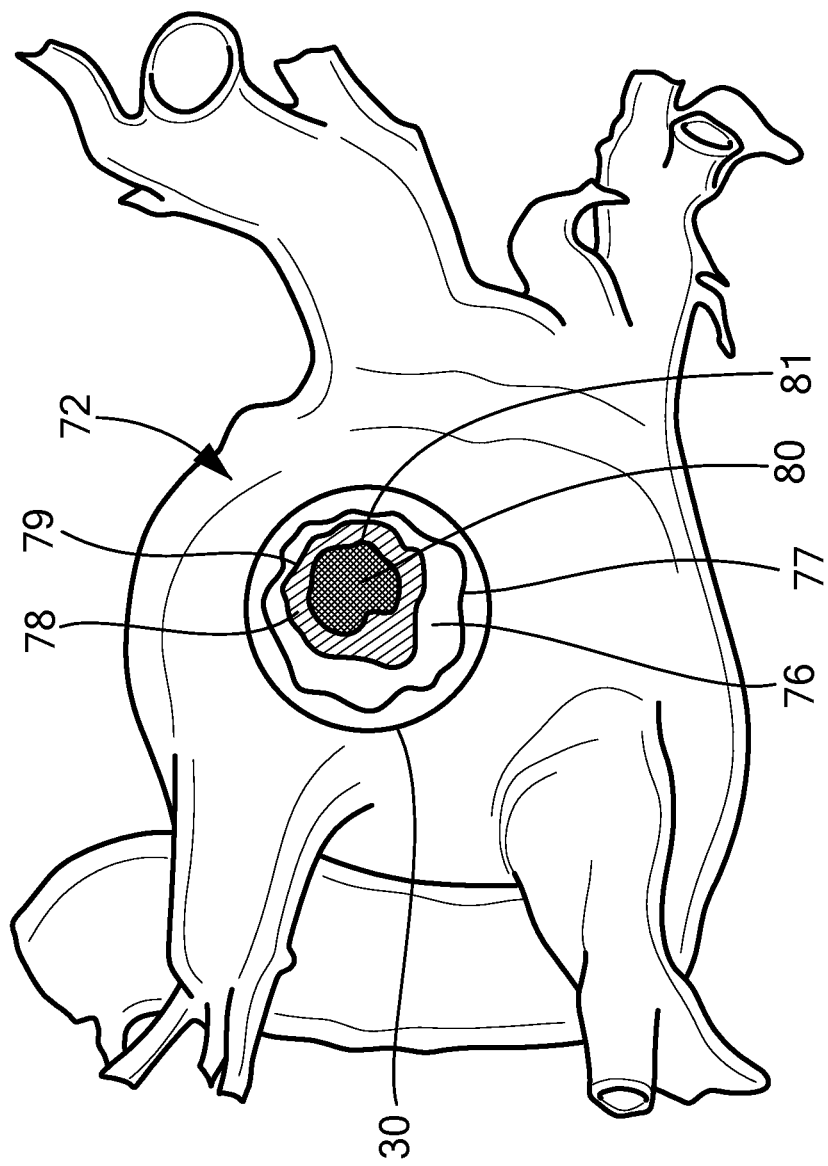

Exemplary endocardial surface maps 72 are shown in FIGS. 3 and 4. The endocardial surface $S_{endo}$ may be shown in a three-dimensional image. In the images shown in FIGS. 3 and 4, for example, the treatment element 30 may be shown in a first color. Areas of the treatment element 30 that are not in contact or are not likely to be in contact (identified as "no contact") 76 and the corresponding isoline 77 may be also be shown in the first color. In other words, the only areas of the treatment element 30 that are shown in a different color, or are otherwise graphically distinguished, from the treatment element 30 are the areas of the treatment element identified as being areas of likely contact 78 and the corresponding isoline 79 and areas of highly probable contact 80 and the corresponding isoline 81. For example, areas of likely contact 78 may be shown in a second color and areas of highly probable contact 80 may be shown in a third color. However, it will be understood that any scheme for differentiating these points may be used.

The endocardial surface map 72 may be continuously refreshed as the device 12 is moved relative to the endocardial surface $S_{endo}$ and/or the image may be captured for display and storage. FIG. 3 shows an endocardial map 72 in which initial contact is detected between the treatment element(s) 30 (here, a spherical or approximately spherical treatment element such as a spherical or approximately spherical balloon) and the endocardial surface $S_{endo}$ is indicated. In FIG. 4, contact between the treatment element(s) 30 and the endocardial surface $S_{endo}$ may increase or improve as the device 12 is maneuvered relative to the target anatomical feature. For example, FIG. 4 shows an increased size of the area identified as highly probable contact 80 and the corresponding isoline 81, meaning contact is improving or has improved.

The processing unit 58 may infer the zone of contact from the position of the device within the heart based on the location(s) of the navigation electrode(s) 38 and the geometry of the treatment element 30 relative to the navigation electrode(s) 38 and the endocardial surface $S_{endo}$. This method may allow devices with arbitrary geometry to be displayed relative to the endocardial surface $S_{endo}$ using a minimal amount of navigation electrode(s) 38. Since the processing unit 58 defines the treatment element geometry entirely as a set of points $(x_n, y_n, z_n)$, these points may be used as reference points to determine a location of the device, thereby reducing the number of required navigation electrode(s) 58. Additionally, the calculated contact regions between the treatment element(s) 30 and the tissue may be qualified with a zone of influence indicator, thus providing the user with a better representation of treatment element-to-tissue contact.

As will be appreciated by one of skill in the art, certain concepts described herein may be embodied as a method, data processing system, and/or computer program product. Accordingly, these concepts described herein may take the form of an entirely hardware embodiment, an entirely software embodiment or an embodiment combining software and hardware aspects. Furthermore, the disclosure may take the form of a computer program product on a tangible computer usable storage medium having computer program code embodied in the medium that can be executed by a computer. Any suitable tangible computer readable medium may be utilized including hard disks, CD-ROMs, electronic storage devices, optical storage devices, or magnetic storage devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for determining a location of a medical device relative to an anatomical feature within a patient's body, the system comprising:
    a medical device including:
        an elongate body having a distal portion, a proximal portion, and a longitudinal axis;
        at least one treatment element coupled to the elongate body distal portion, the at least one treatment element having an outer surface defining a surface geometry; and
        at least a first navigation electrode and a second navigation electrode configured to convey an electrical signal and coupled to the elongate body distal portion; and
    a navigation system in communication with at least the first navigation electrode and the second navigation electrode, the navigation system including a processing unit having processing circuitry programmed to:
        determine a first surface of the anatomical feature in an anatomical image of the anatomical feature, the anatomical image being accessible by the processing circuitry;
        determine a spatial location of at least the first navigation electrode and the second navigation electrode;
        access a database containing geometrical information about the surface geometry of the at least one treatment element relative to the at least the first navigation electrode and the second navigation electrode;
        calculate the surface geometry of the at least one treatment element by using the geometrical information obtained from the database to parameterize the surface geometry of the at least one treatment element relative to the at least the first navigation electrode and the second navigation electrode;
        map the surface geometry of the at least one treatment element relative to the at least the first navigation electrode and the second navigation electrode;
        define the surface geometry of the at least one treatment element with a plurality of points on the surface geometry of the at least one treatment element;
        for each of the plurality of points on the surface geometry of the at least one treatment element defined by the processing circuitry, define a corresponding point on the first surface of the anatomical feature that is closest to the point of the plurality of points on the surface geometry of the at least one treatment element;
        for each defined corresponding point on the first surface of the anatomical feature, assign a value indicating likelihood of contact between the defined point on the first surface of the anatomical feature and the point of the plurality of points on the surface geometry of the at least one treatment element, the value indicating likelihood of contact being one of:
            highly probable contact,
            likely contact, and
            no contact; and assign the value of highly probable contact to a defined point on the first surface of the anatomical feature when a distance between the defined point on the first surface of the anatomical feature and the nearest point of the plurality of points on the surface geometry of the at least one treatment element is less than a first predetermined distance;

assign the value of likely contact to a defined point on the first surface of the anatomical feature when a distance between the defined point on the first surface of the anatomical feature and the nearest point of the plurality of points on the surface geometry of the at least one treatment element is between the first predetermined distance and a second predetermined distance, the first predetermined distance being less than the second predetermined distance; and display a map of at least the first surface of the anatomical feature, the map including at least one isoline corresponding to the value indicating likelihood of contact for at least one of the defined corresponding points on the first surface of the anatomical feature.

2. The system of claim 1, wherein the first navigation electrode is distal to the at least one treatment element and the second navigation electrode is proximal to the at least one treatment element.

3. The system of claim 2, wherein the at least one treatment element is an expandable treatment element.

4. The system of claim 3, wherein the expandable treatment element is a spherical balloon.

5. The system of claim 3, wherein the expandable treatment element is a cylindrical balloon.

6. The system of claim 2, wherein the at least one treatment element is an expandable array of electrodes.

7. The system of claim 2, wherein the at least one treatment element is a plurality of treatment elements located over a linear distance.

8. The system of claim 1, wherein the processing circuitry is further programmed to store an anatomical image of an area including the anatomical feature.

9. The system of claim 8, wherein the processing circuitry is programmed to determine the first surface of the anatomical feature based on the anatomical image.

10. The system of claim 8, wherein the processing circuitry is further programmed to determine a second surface of the anatomical feature, the second surface being opposite the first surface, the processing circuitry being configured to determine the first surface based on the second surface.

11. The system of claim 1, wherein the first predetermined distance is 0.5 mm and the second predetermined distance is 1.0 mm.

12. The system of claim 1, wherein the processing circuitry is further programmed to estimate the likelihood of contact by assigning the value on a continuous scale to each defined point on the first surface of the anatomical feature, the value being one of:
a minimum value indicating no contact;
a maximum value indicating definite contact; and
an intermediate value between the minimum value and the maximum value along the continuous scale, the intermediate value indicating possible contact with a varying degree of certainty.

13. A system for determining a location of a medical device relative to an anatomical feature, the system comprising:
a medical device including:
an elongate body having a distal portion, a proximal portion, and a longitudinal axis;
at least one treatment element coupled to the elongate body distal portion, the at least one treatment element having an outer surface defining a surface geometry; and
a first navigation electrode coupled to the elongate body distal portion distal to the at least one treatment element and a second navigation electrode coupled to the elongate body distal portion proximal to the at least one treatment element, the first and second navigation electrodes configured to convey an electrical signal; and
a navigation system in communication with the first navigation electrode and the second navigation electrode, the navigation system being configured to store an anatomical image of an area including the anatomical feature, the navigation system including a processing unit having processing circuitry with a memory and a processor, the memory in communication with the processor and having instructions that, when executed by the processor, configure the processor to:
determine a first surface of the anatomical feature and a second surface of the anatomical feature that is opposite the first surface, the processor being configured to determine the first surface based on one of:
the anatomical image; and
transformation of the second surface;
determine a spatial location of each of the first navigation electrode and the second navigation electrode;
access a database containing geometrical information about the surface geometry of the at least one treatment element relative to the first navigation electrode and the second navigation electrode;
calculate the surface geometry of the at least one treatment element by using the geometrical information obtained from the database to parameterize the surface geometry of the at least one treatment element relative to the first navigation electrode and the second navigation electrode;
map the surface geometry of the at least one treatment element relative to the first navigation electrode and the second navigation electrode;
define the surface geometry of the at least one treatment element with a plurality of points on the surface geometry of the at least one treatment element;
for each of the plurality of points on the surface geometry of the at least one treatment element defined by the processor, define a corresponding point on the first surface of the anatomical feature that is closest to the point of the plurality of points on the surface geometry of the at least one treatment element;
for each defined corresponding point on the first surface of the anatomical feature, assign a value indicating likelihood of contact between the defined point on the first surface of the anatomical feature and a corresponding point of the plurality of points on the surface geometry of the at least one treatment element, the value being one of:
a minimum value indicating no contact;
a maximum value indicating definite contact; and
an intermediate value between the minimum value and the maximum value along a continuous scale, the intermediate value indicating possible contact with a varying degree of certainty, with the degree of certainty being less when the intermediate value is closer to the minimum value than when the intermediate value is closer to the maximum value; and display a map of at least the first surface of the anatomical feature, the map including at least one isoline corresponding to the value assigned to each defined corresponding point.

\* \* \* \* \*